United States Patent
Martin et al.

(10) Patent No.: US 8,546,142 B2
(45) Date of Patent: Oct. 1, 2013

(54) REVERSE FLOW PERFUSION OF THREE-DIMENSIONAL SCAFFOLDS

(75) Inventors: Ivan Martin, Oberwil (CH); David Wendt, Arlesheim (CH); Alessandra Braccini, Basel (CH); Rodolfo Quatro, Genoa (IT); Marcel Jakob, Andwil (CH)

(73) Assignee: Millenium Biologix Technologies Inc., Kingston, Ontario (CA)

( * ) Notice: Subject to any disclaimer, the term of this patent is extended or adjusted under 35 U.S.C. 154(b) by 1300 days.

(21) Appl. No.: 11/658,751

(22) PCT Filed: Mar. 4, 2005

(86) PCT No.: PCT/CA2005/000334
§ 371 (c)(1),
(2), (4) Date: Oct. 19, 2007

(87) PCT Pub. No.: WO2005/085429
PCT Pub. Date: Sep. 15, 2005

(65) Prior Publication Data
US 2008/0318315 A1 Dec. 25, 2008

Related U.S. Application Data

(60) Provisional application No. 60/549,931, filed on Mar. 5, 2004.

(51) Int. Cl.
*C12N 5/00* (2006.01)

(52) U.S. Cl.
USPC ............... 435/395; 435/293.1; 435/304.1; 435/298.1

(58) Field of Classification Search
None
See application file for complete search history.

(56) References Cited

U.S. PATENT DOCUMENTS 6,323,146 B1 * 11/2001 Pugh et al. .................. 501/1
7,033,823 B2 * 4/2006 Chang .................... 435/297.2

FOREIGN PATENT DOCUMENTS

| WO | 01/02030 A2 | 1/2001 |
| WO | 01/48153 A1 | 7/2001 |
| WO | 03/089566 A1 | 10/2003 |

OTHER PUBLICATIONS

Freed et al. Microgravity tissue engineering. In Vitro Cellular & Developmental Biology. Animal, vol. 33, No. 5, pp. 381-385, May 1997.*
Goldstein et al, Biomaterials, (2002) vol. 22, pp. 1279-1288.*
Wendt, A. et al.,"Oscillating Perfusion of Cell Suspensions Through Three-Dimensional Scaffolds Enhances Cell Seeding Efficiency and Uniformity," *Biotechnol Bioeng.*, vol. 84, pp. 205-214, (2003).
Radisic, M. et al.,"Medium perfusion enables engineering of compact and contractile cardiac tissue," *AM J Physiol Heart Circ Physiol.*, vol. 286, pp. H507-H516, (2004).
Sodian, R. et al.,"Tissue-Engineering Bioreactors: A New Combined Cell-Seeding and Perfusion System for Vascular Tissue Engineering," *Tissue Eng.*, vol. 8, No. 5, pp. 863-870, (2002).
Raimondi, M. T. et al.,"The effect of media perfusion on three-dimensional cultures of human chondrocytes: Integration of experimental and computational approaches," *Biorheology*, vol. 41, No. 3-4, pp. 401-410, (2004).

(Continued)

*Primary Examiner* — Allison Ford
(74) *Attorney, Agent, or Firm* — Nath, Goldberg & Meyer; Tanya E. Harkins (57) ABSTRACT

The invention is a reverse-flow method and system for the loading, proliferation and differentiation of cells into and throughout an implantable biocompatible three-dimensional scaffold.

26 Claims, 6 Drawing Sheets (56) References Cited

OTHER PUBLICATIONS

Martin, I. et al., "The role of bioreactors in tissue engineering," *Trends Biotechnol*, vol. 22, No. 2, pp. 80-86, (2004).

Bancroft, G.N. et al., "Design of a Flow Perfusion Bioreactor System for Bone Tissue-Engineering Applicatons," *Tissue Eng.*, vol. 9, No. 3, pp. 549-554, (2003).

Kim, S.S. et al., "Dynamic Seeding and in Vitro Culture of Hepatocytes in a Flow Perfusion System," *Tissue Eng.*, vol. 6, No. 1, pp. 39-44, (2000).

Wang, H.J., et al., "Tissue engineering of dermal substitutes based on porous PEGT/PBT copolymer scaffolds: comparison of culture conditions", *Journal of Materials Science: Materials in Medicine*, vol. 14, No. 3, pp. 235-240, (2003).

* cited by examiner

REVERSE FLOW PERFUSION OF THREE-DIMENSIONAL SCAFFOLDS

This application claims priority under 35 U.S.C. §119(e) to U.S. Provisional Application No. 60/549,931 filed on Mar. 5, 2004, the contents of which are hereby incorporated by reference in there entirety.

FIELD OF THE INVENTION

The present invention relates to a method and system for providing cells within a three-dimensional scaffold. More specifically, the invention is a reverse-flow method and system for the loading, culturing and expansion of cells into and throughout an implantable three-dimensional scaffold.

BACKGROUND OF THE INVENTION

Tissue engineering aims at the development of biological substitutes that restore, maintain or improve tissue function (Langer & Vacanti J. P. Tissue Engineering. Science. 260: 920-926, 1993). One strategy currently adopted to regenerate new tissues such as skin, cartilage or bone, is the isolation, in vitro expansion and loading into a three-dimensional scaffold the expanded cells (Brittberg M. et al., Treatment of deep articular cartilage defects in the knee with autologous chondrocyte transplantation. N Engl J Med 331:889-895.1994; Quarto R. et al., Repair of large bone defects with the use of autologous bone marrow stromal cells. N Engl J Med 344: 385-386, 2001; Rheinwald J. G. et al., Serial cultivation of strains of human epidermal keratinocytes: the formation of keratinizing colonies from single cells. Cell 6:331-344, 1975).

Bone marrow stromal cells (BMSC) have been used for the regeneration of bone and have been demonstrated to be expandable in monolayers from a marrow aspirate and, when loaded into a porous ceramic scaffold after expansion, are capable of generating an osteoinductive construct which supports bridging of large segmental defects in human (Quarto R. et al., Repair of large bone defects with the use of autologous bone marrow stromal cells. N Engl J Med 344:385-386, 2001).

A bioreactor has been developed allowing for the perfusion of cell suspensions through three-dimensional porous scaffolds (Wendt D. et al., Oscillating perfusion of cell suspensions through three-dimensional scaffolds enhances cell seeding efficiency and uniformity. Biotechnol Bioeng, 84:205-214, 2003). Cells were isolated from a cartilage biopsy or bone marrow aspirate and expanded in monolayers prior to use in the bioreactor. Controlled perfusion of BMSC, initially expanded in monolayers, has been demonstrated to increase the capacity of cells to differentiate and deposit mineralized matrix (Bancroft G. N. et al., Fluid flow increases mineralized matrix deposition in 3D perfusion culture of marrow stromal osteoblasts in a dose-dependent manner. Proc Natl Acad Sci USA 99:12600-12605, 2002). It has also been demonstrated that BMSC can be expanded in suspension cultures in spinner flasks, however, the disclosed method did not involve association of the expanded cells to a three-dimensional scaffold (Baksh D. et al., Adult human bone marrow derived mesenchymal progenitor cells are capable of adhesion independent survival and expansion. Exp Hematol 31:723-732, 2003).

GB Patent Application 2 178 447 discloses a cultivation system for cell attachment using a matrix material in which cells are proliferated along fibers of a sheet in three dimensions. The matrix material is provided in a configuration as a reactor through which separate conduits are placed therethrough, one conduit for the supply and/or removal of liquid medium, and the other for providing a supply of gases.

U.S. Pat. No. 6,372,495 discloses a reactor in which cells are seeded and allowed to distribute throughout the reactor and adhere to a solid support. The reactor is rotated along its longitudinal axis to distribute cells throughout the reactor to prevent the formation of a cell pellet. The cells are thus allowed to follow a circular path through the reactor so that the cells repeatedly come into contact with the matrix material and get entrapped therein.

While the aforementioned disclose various methods for seeding cells to a three-dimensional scaffold, it is desirable to develop a method and system that increases the efficiency and consistency of cell loading throughout a three-dimensional scaffold such that the cells can further expand in a more even manner throughout the scaffold, thus producing a more desirable tissue implant.

SUMMARY OF THE INVENTION

The present invention is a novel method and system for the direct culture of cells substantially throughout a three-dimensional biocompatible porous scaffold, allowing the cells to proliferate and differentiate directly within and throughout the scaffold. The method is a reverse-flow perfusion method which directly seeds cells substantially throughout a desired three-dimensional biocompatible scaffold such that the cells proliferate and differentiate therein and form an implantable device. Reverse perfusion to load the cells helps to increase cellular/scaffold interactions resulting in the better seeding. Furthermore, reverse perfusion minimizes the loss of cells and cellular expressed factors from within the scaffold thereby facilitating proliferation, differentiation and the local expression and retention of extracellular matrix molecules. It is noted that reverse perfusion is one aspect of the present invention and the invention further encompasses many combinations of sequences as well as multi-directional flow.

The method and system of the invention provide for substantially continuous cell seeding within a three-dimensional scaffold in substantially opposite directions of flow through the scaffold. This results in a three-dimensional scaffold that is more evenly loaded with cells so that as the cells proliferate and differentiate throughout the scaffold in a more consistent manner, an improved implant is provided. Furthermore, the cells are substantially continuously seeded through the scaffold in two or more directions over a period of time. In this manner, initially seeded cells start to proliferate and differentiate within the scaffold while additional cells continue to be seeded throughout. The resultant three-dimensional implant is thus more consistent with respect to the provision of cells and tissue throughout so that the implant will have improved capabilities of integrating in vivo.

According to an aspect of the present invention is a method for loading cells directly throughout a three-dimensional porous scaffold, the method comprising;

continuously perfusing a volume of cells in alternate directions through a porous three-dimensional scaffold for a period of time sufficient for said cells to seed within said scaffold and proliferate throughout said scaffold.

According to an aspect of the present invention is a method for loading cells directly throughout a three-dimensional porous scaffold, the method comprising;

intermittently perfusing a volume of cells in alternate directions through a porous three-dimensional scaffold for a period of time sufficient for said cells to seed within said scaffold and proliferate throughout said scaffold.

According to an aspect of the present invention is a method for loading cells directly throughout a three-dimensional porous scaffold, the method comprising;

(a) perfusing a volume of cells at a first velocity through said scaffold in a first direction and then in a second direction through said scaffold, wherein said second direction is substantially opposite to said first direction;

(b) repeating (a) for a period of time sufficient for said cells to seed and proliferate throughout said scaffold; and (c) repeating (a) at a second velocity, which is less than said first velocity, for a further period of time sufficient for said cells to differentiate throughout said scaffold.

In aspects of the invention, once the cells are seeded and proliferating, the velocity is decreased for a further time period allowing for the seeded and proliferated cells to differentiate.

According to another aspect of the present invention is a method for loading cells directly throughout a three-dimensional porous scaffold, the method comprising;

continuously perfusing a volume of cells in alternate directions through a porous three-dimensional scaffold at a first velocity for a sufficient time for said cells to seed within said scaffold and proliferate throughout said scaffold; and reducing said velocity of said volume of cells to less than said first velocity for a further time period sufficient to continue said seeding and proliferation of said cells and differentiation of said cells throughout said scaffold.

According to yet another aspect of the invention is a method for making an osteoinductive three-dimensional implant, the method comprising;

(a) perfusing a volume of BMSC and at a first velocity in a first and second direction through said scaffold, wherein said second direction is substantially opposite to said first direction;

(b) repeating (a) at a second velocity which is less than said first velocity;

(c) repeating (b) for a period of time sufficient for said BMSC to seed, proliferate and differentiate throughout said scaffold.

According to still a further aspect of the invention is a method for making an osteoinductive three-dimensional implant, the method comprising;

perfusing a volume of bone marrow nucleated cells in substantially alternate directions through a porous three-dimensional scaffold for a period of time sufficient for said bone marrow nucleated cells to seed and proliferate and differentiate into osteoprogenitor cells throughout said scaffold forming said implant.

According to another aspect of the present invention is a method for making a three-dimensional tissue implant comprising expanded cells provided essentially substantially throughout said implant, the method comprising;

(a) perfusing cells in alternate directions through a porous three-dimensional scaffold without prior expansion to load said cells within said scaffold; and (b) repeating (b) for a time period sufficient for said cells to proliferate and differentiate to form said implant.

In aspects, (b) is conducted at lower velocities than (a).

Still in other aspects of the invention is a perfusion system for seeding and proliferating cells throughout a three-dimensional scaffold, the system comprising;

a three-dimensional scaffold supported within a chamber; and a means for perfusing a volume of cells in different directions through said scaffold.

In aspects, the perfusion system also has a means for varying the velocity of the cells that are being perfused.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE DRAWINGS

The present invention will become more fully understood from the description given herein, and from the accompanying drawings, which are given by way of illustration only and do not limit the intended scope of the invention.

DETAILED DESCRIPTION OF THE PREFERRED EMBODIMENTS

The invention is a novel method and system for seeding cells throughout a porous scaffold in a manner that seeds the cells essentially consistently throughout the scaffold allowing the cells to proliferate and differentiate throughout the scaffold. Furthermore, the method is a substantially continuous reverse-flow perfusion method that seeds cells throughout a biocompatible porous scaffold such that even when cells have already seeded within the scaffold and started to proliferate and differentiate, further cells are still continuously being still seeded through the scaffold. In this manner, a reproducible and more consistent three-dimensional implant is provided that has better properties for integration in vivo.

The method is reliable and relatively simple. The method involves perfusing a volume of cells through a biocompatible porous scaffold first in one direction and then substantially immediately followed by perfusion of the volume of cells in the other direction (i.e. reverse-flow). This is done in a continuous manner for varying times such as several days until a desired end-result implant is achieved. As the volume of cells is being perfused in each direction, the cells seed (i.e. load) within the pores of the porous scaffold and begin to proliferate and later differentiate throughout the scaffold. The provision of the reverse flow helps to ensure cells seed more consistently throughout the porous scaffold which is a major obstacle with seeding methods of the prior art. Because more cells are seeded and continue to seed during a period of perfusion, more cells are retained throughout the porous scaffold. The cells more successfully proliferate and differentiate due to the fact that the retained cells express various growth factors that remain in the milieu of the proliferating and differentiating cells. Over a period of time the seeded cells will therefore proliferate and differentiate in a manner such that substantially the entire porous scaffold has differentiated cells therein increasing the likelihood that the resultant implant will be readily integrated in vivo.

It is understood that the reverse flow-perfusion may be conducted continuously or intermittently (i.e. in a more pulsatile manner) as is desired. It is also understood by one of skill in the art that the reverse-flow perfusion through the porous scaffold need not be exactly along a single axis (i.e. 180° C.). The objective is to introduce flow vectors in two or more directions relative to the scaffold such that all surfaces of the scaffold have the potential for cell scaffold contact and resulting cell attachment.

The method of the invention also encompasses multi-directional flow along different axis through the scaffold. It is understood however, that multi-directional flow may be obtained by rotation or other movement of the scaffold. Such rotation or movement also generates flow.

Cells for use in the present invention are selected depending on the end use of the generated implant. In aspects of the invention the cells are BMSC in order that an osteoinductive tissue implant is generated. It is within the scope of the invention to use a variety of different cell types such as but not limited to bone marrow stromal cells (BMSC), adipose derived stem cells (ADSC), periosteal cells, chondrocytes, osteoblasts, myoblasts, hepatocytes, urothelial cells and other attachment dependent cells. It is also within the scope of the present invention to use a combination of different types of cells as desired for the reverse-perfusion of the porous three-dimensional scaffold. The combination of cells can be provided as a single cell mixture volume. Alternatively, a first population of cells can be initially used in the method for a selected period of time followed by the use of a different cell population to the first for a next selected period of time, and so on as desired. In this manner, the porous scaffold can be successively seeded with a variety of cell types as is desired to achieve an implant. It is understood that each successive seeding of different cell types can be conducted at different flow velocities, different times and at a different axis.

The method of the invention allows for the seeding of cells prior to their proliferation or differentiation. For example, bone marrow nucleated cells may be directly seeded using the method of the invention within a scaffold. These cells can then differentiate into osteoprogenitor cells that further proliferate within the scaffold to form an implant suitable for bone repair. Thus the invention encompasses the use of a variety of undifferentiated cells for seeding, proliferating and differentiating within the scaffold to form a desired implant (i.e. tissue construct).

The cells are provided in any suitable cell culture media as is understood by one of skill in the art. The culture media may be selected dependent on the cell type for example. The culture media may be obtained from any commercial source. It is also understood that any selection of biological (i.e. proteins, growth factors, etc.) or pharmaceutical agents may be further included with the cells as provided as a volume of suspended cells. The cells may be derived from any source such as for example a tissue biopsy, a cell or marrow aspirate, an in vitro cell culture and/or a known commercially available cultured cell line.

The volume and number of cells that are reverse-perfused through the porous scaffold is not restricted in the present invention.

In aspects of the invention the cells may be perfused at velocities of about 1 mm/sec for a first time period and then a different selected velocity for a second time period. In aspects of the invention, a slower velocity for the perfusion is desirous for the second time period. The selection of a slower perfusion velocity for the later part of the reverse perfusion may help to ensure that the seeded cells, which are undergoing proliferation and differentiation, are not substantially "dislodged" from the scaffold or substantially negatively affected. One of skill in the art would understand the range of perfusion velocities for use in the method of the present invention can be for example about 0.001 mm/sec to about 10 mm/sec and range thereinbetween. It is also understood by one of skill in the art that a change in velocity may be progressive with respect to the loading of cells and with each pass through the scaffold.

The porous scaffold for use in the present invention can be of any desired material and porosity depending on the end use. For example in aspects of the invention where an osteoinductive implant is desired, the porous scaffold may be formed from a material selected from the group consisting of biocompatible metallics, ceramics (including hydroxyapatite and calcium hydroxyapatite), polymers, and composite materials consisting of phosphate(s), bioactive glass(es), bioresorbable polymer(s), biocompatible metals and metallic alloys as well as combinations of such materials.

The scaffold may be fabricated from a calcium phosphate material Skelite™ that is described in U.S. Pat. No. 6,323,146 (the disclosure of which is incorporated herein by reference in its entirety). Briefly, the calcium phosphate material described in U.S. Pat. No. 6,323,146 is an isolated bioresorbable biomaterial compound comprising calcium, oxygen and phosphorous, where a portion of at least one of these elements is substituted with an element having an ionic radius of approximately 0.1 to 0.6 Å. In further aspects, the biomaterial compound has the formula: $(Ca_{1-w}A_{w})_{i}[(P_{1-x-y-z}B_{x}C_{y}D_{z})O_{j}]_{2}$ wherein A is selected from those elements having an ionic radius of approximately 0.4 to 1.1 Å; B, C and D are selected from those elements having an ionic radius of approximately 0.1 to 0.4 Å; w is greater than or equal to zero but less than 1; x is greater than or equal to zero but less than 1; y is greater than or equal to zero but less than 1; z is greater than or equal to zero but less than 1; x+y+z is greater than zero but less than 1; i is greater than or equal to 2 but less than or equal to 4; and j equals 4−δ, where δ is greater than or equal to zero but less than or equal to 1.

The scaffold may contain additional biological materials such as collagen, proteoglycans and other proteins/peptides etc. as is understood to one of skill in the art. One group of useful peptides are described in PCT CA03/00634 (the disclosure of which is incorporated herein in its entirety by reference), these peptides are referred to as "BCSP" designating "bone and cartilage stimulating peptides".

To optimize the growth or the performance of the cells in the scaffold it may be desired to provide additional stimulation to the scaffold in the bioreactor in the form of a mechanical load, pressure, electrical, chemical or other stimuli. This can be accomplished by the provision of an actuator or a probe in operable communication with the scaffold.

One of skill in the art would readily understand that the size and shape of the scaffold is selected depending on the desired size of implant required for a particular in vivo or ex vivo application. Depending on the application the scaffold can be a solid porous block of a fixed shape or a volume made up of particles which can be directly used or shaped to the required form prior to implantation.

Figure 1:
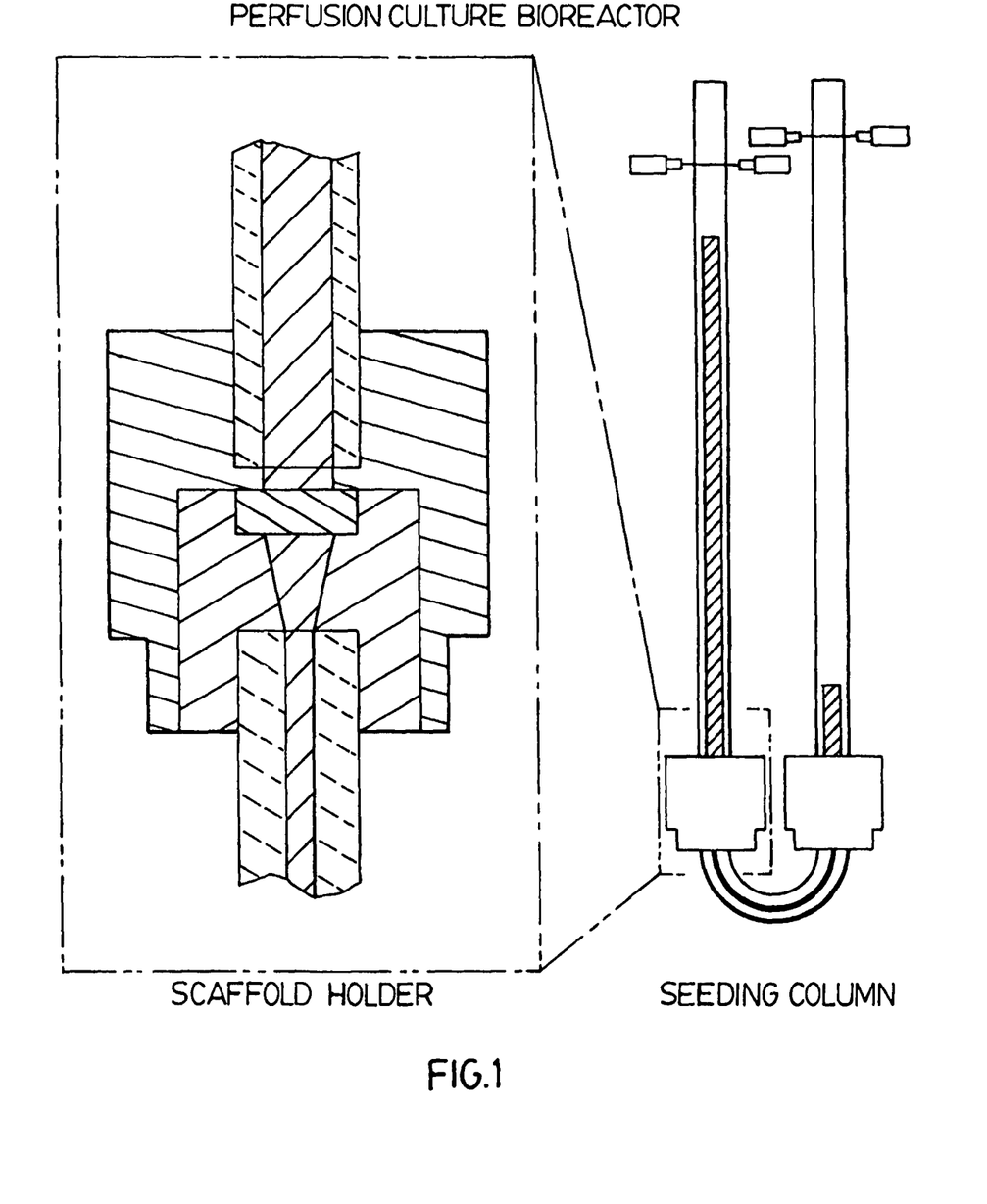
FIG. 1 shows one embodiment of the perfusion system of the present invention.

A representative example of a system of the invention is shown in FIG. 1. The system is shown as an elongated U-shaped column having a supported scaffold therein. It is understood that a scaffold can be provided on both extended portions of the column as shown in FIG. 1, alternatively, only one scaffold may be used. The column is shown to have sensors that sense the flow of the volume of cells such that once the volume is reached in the column, a reverse flow of the volume of cells is then generated. This may be accomplished by operatively connecting the sensors to a remote or integral computerized pump system as is understood by one of skill in the art. Furthermore, sensors may be used to monitor the growth of cells in the scaffold and provide nutrients in the form of fresh medium at the optimal times. Sensors which may be used include but are not limited to those to measure oxygen and pH levels. In a clinical application, an automation system that controls the entire process from the addition of the cells to the finished culturing of the scaffold may be implemented to achieve the necessary reliability and practicality for routine clinical use.

While the system is shown to comprise a U-shaped column it is understood that variations to the system are within the scope of the present invention so long as the reverse-perfusion aspect is maintained. For example, the elongated column can be essentially one long continuous straight column having a porous scaffold supported therein with sensors present at each end of the pipe such that the continuous reverse-flow of the volume of cells is in a horizontal manner rather than as vertically shown in FIG. 1. Other designs are also within the scope of the present invention. Furthermore, various bioreactor devices for seeding and culturing tissue engineered implants may be used within the system of the invention such as but not limited to those shown in FIG. 4 or 5. The bioreactors contain the scaffold to be perfused with cells.

In one representative embodiment of the invention, BMSC are seeded within a hydroxyapatite porous scaffold to provide an osteoinductive implant.

In summary, the present invention provides for the consistent and substantially even loading of cells within biocompatible porous scaffolds in a manner that allows for the proliferation and differentiation of the cells therein. As such, the resultant scaffold contains cells and tissue throughout leading to its use as an implant.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Loading of BMSC Throughout a Porous Scaffold

Figure 2A:
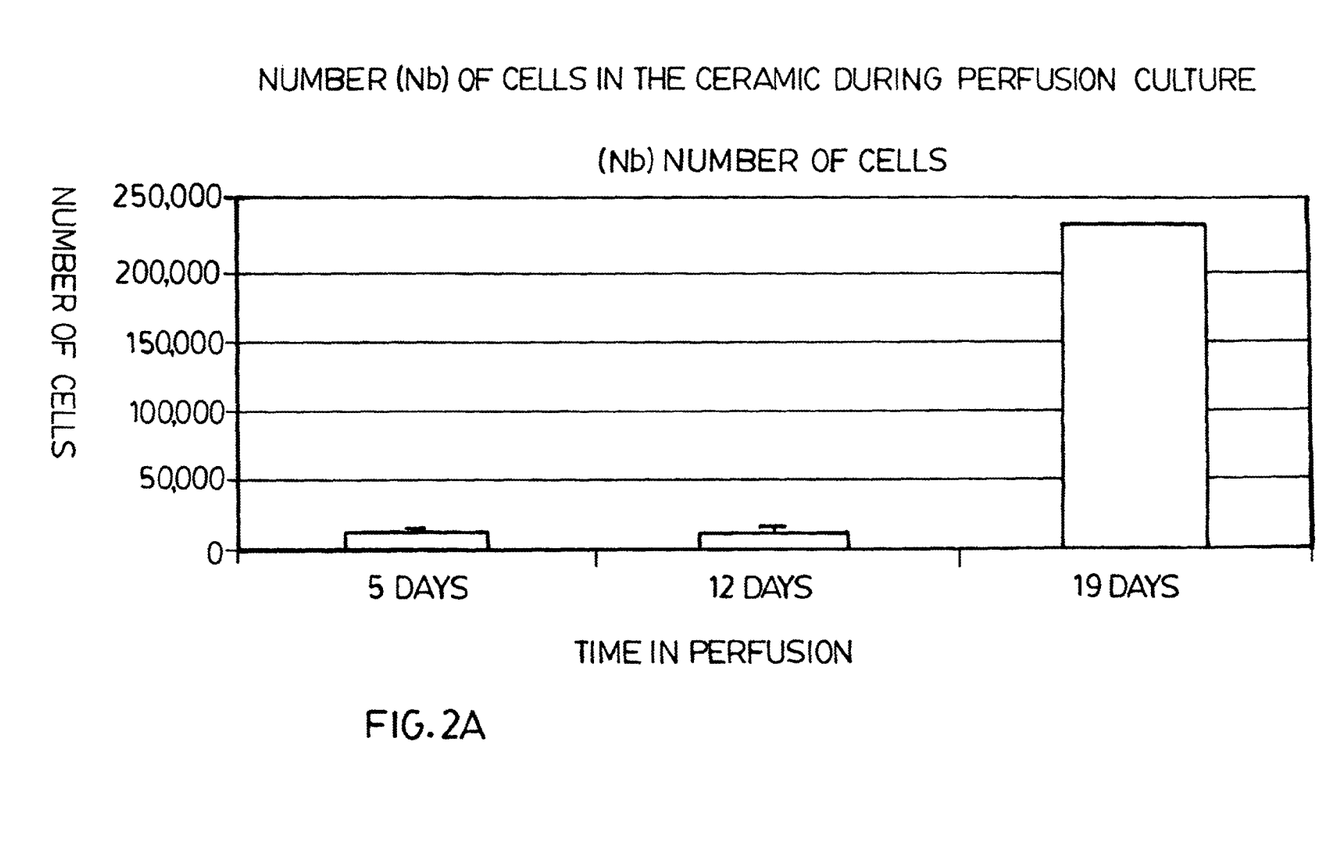
FIG. 2A shows the number of BMSC attached to the scaffold during perfusion.
Figure 2B:
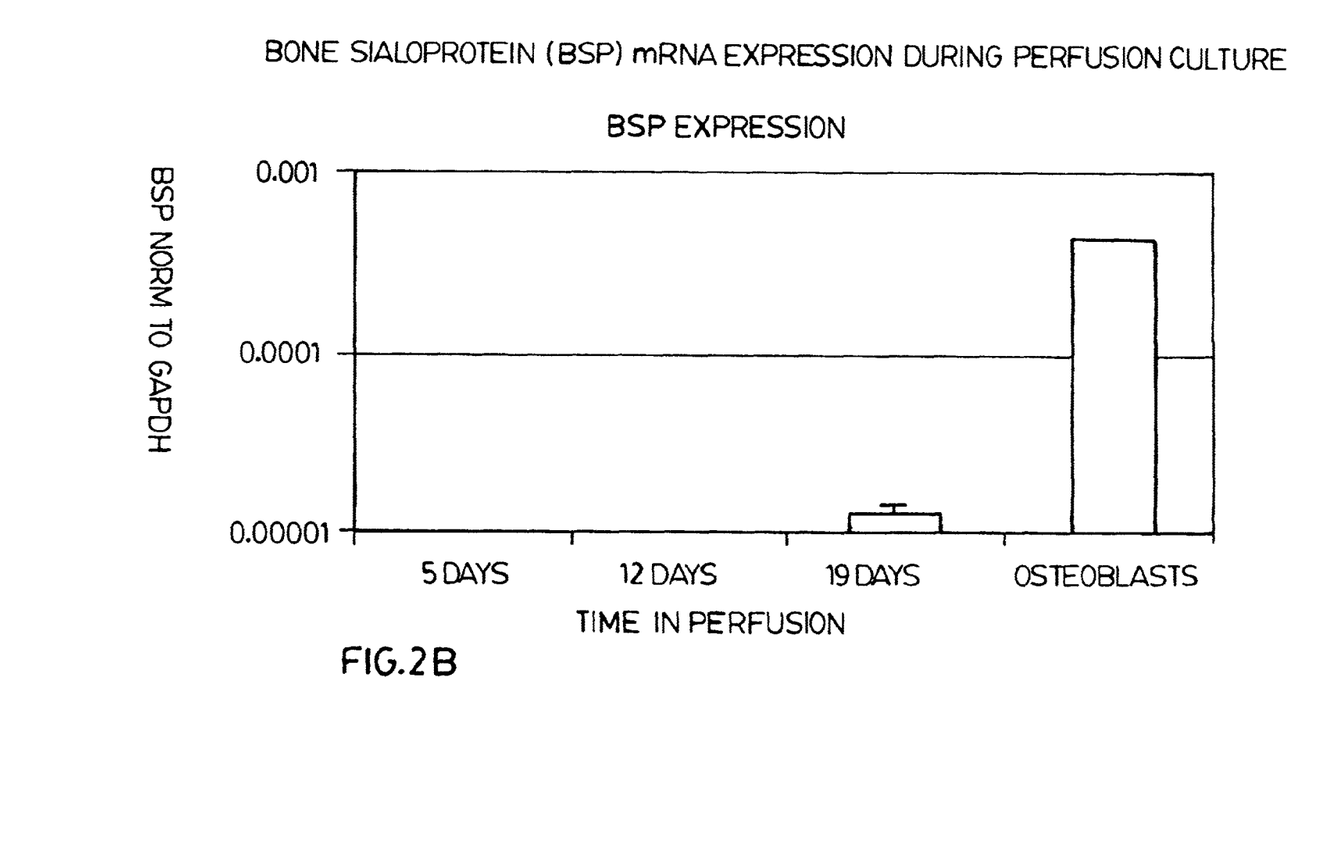
FIG. 2B shows the expression of bone sialoprotein (BSP) mRNA expression of the BMSC during time periods of the perfusion.
Figure 2C:
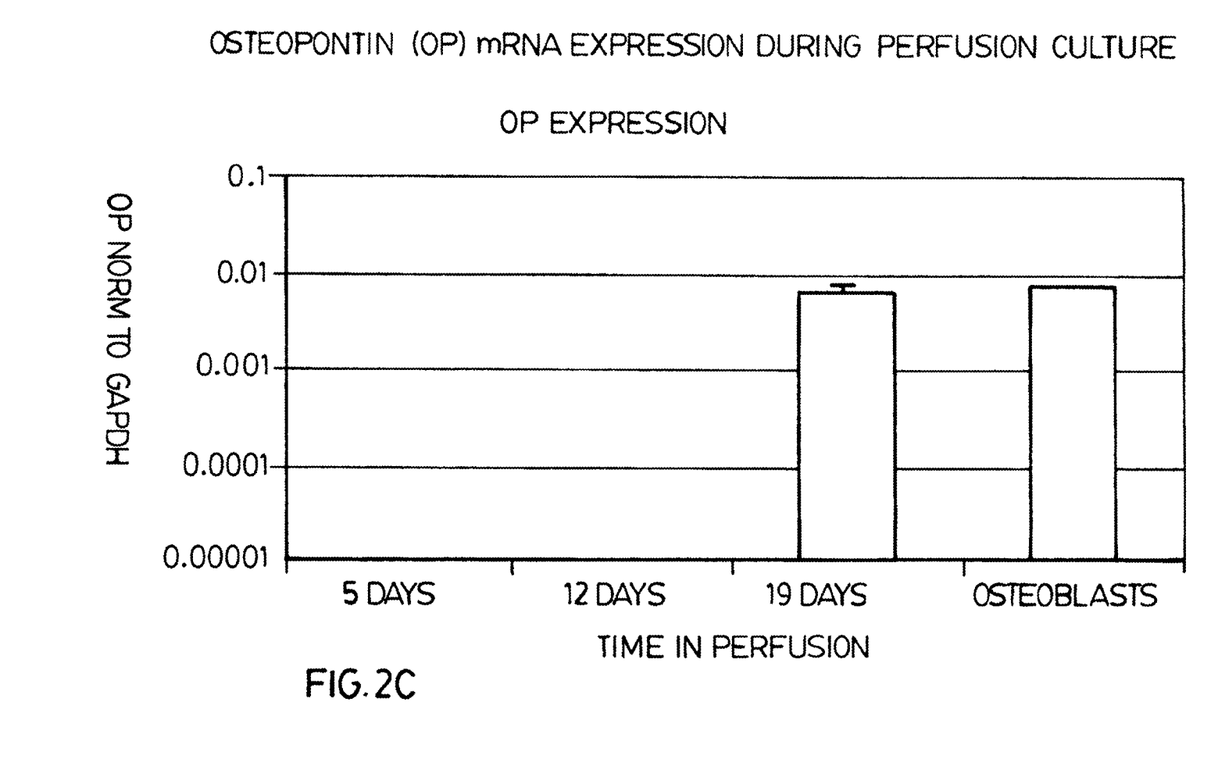
FIG. 2C shows the expression of osteopontin (OP) mRNA expression of the BMSC during time periods of the perfusion.
Figure 3A:
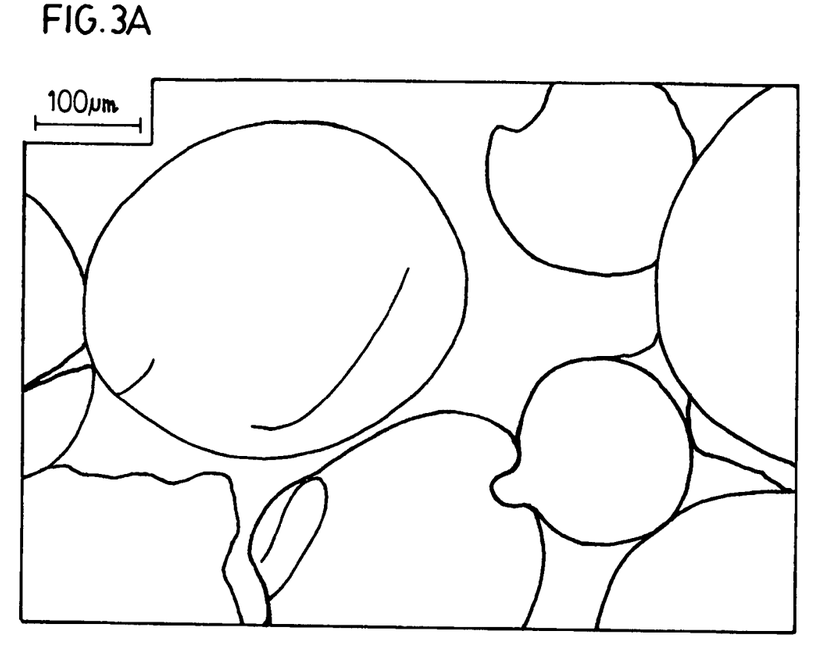
FIG. 3A shows the histological appearance of implanted ceramic scaffold where the BMSC were cultured under perfusion for up to 12 days. Only fibrous tissue was formed.
Figure 3B:
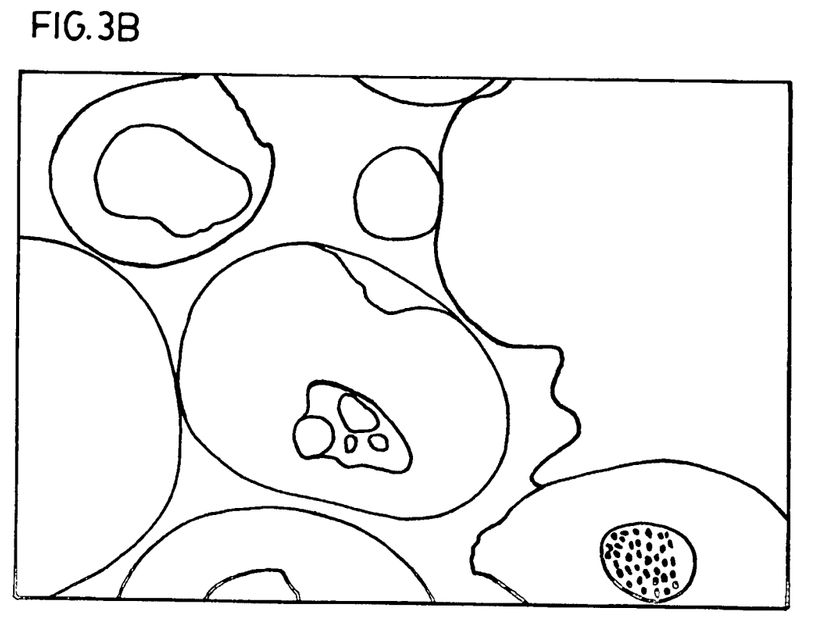
FIG. 3B shows the histological appearance of implanted ceramic scaffold where the BMSC were cultured under perfusion for 19 days. The pores of the ceramic are filled with bone tissue.

Nucleated cells from human bone marrow were perfused in alternate directions through the pores of a hydroxyapatite foam at superficial velocities of 1 mm/sec for the first 5 days and of 0.1 mm/sec for the subsequent 15 days using a perfusion system shown in FIG. 1. The BMSC attached to the ceramic and proliferated with time in culture (FIG. 2A). The cells expressed osteoblast-related genes, including bone sialoprotein and osteopontin (FIGS. 2B, 2C). When tested subcutaneously in nude mice, the cell-loaded porous ceramic scaffolds were found to induce ectopic formation of bone after 20 days in culture (FIGS. 3A, 3B).

Example 2

Bioreactor Device for Seeding and Culturing Tissue Engineered Implants

Figure 4:
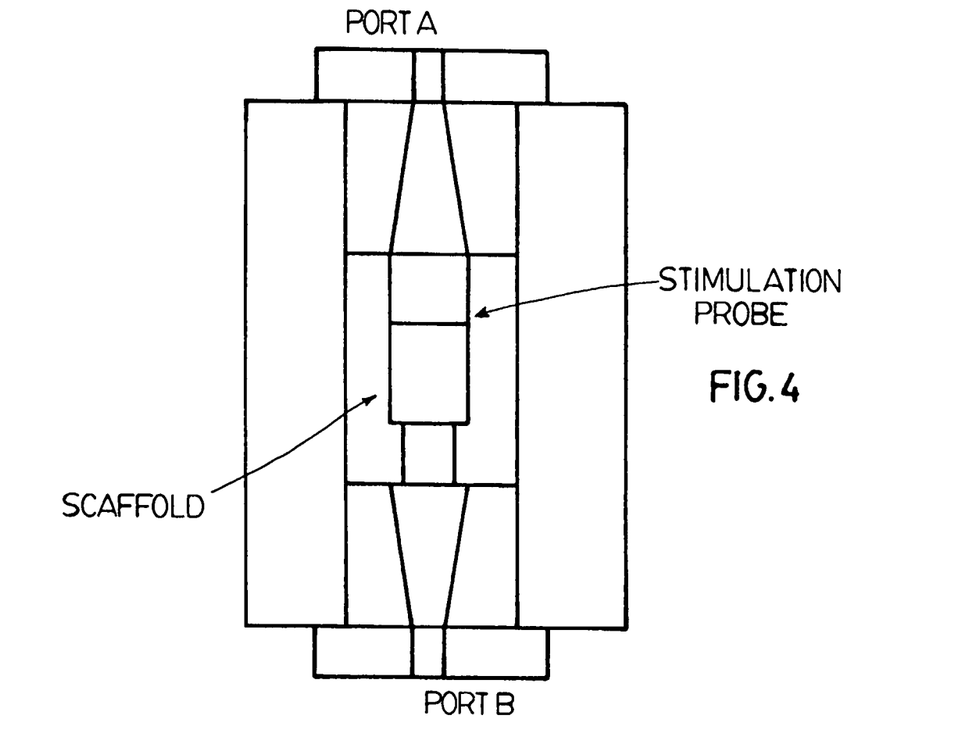
FIG. 4 shows a bioreactor device for seeding and culturing tissue engineered implants.

FIG. 4 shows a bioreactor device into which is loaded a suitable scaffold for the growth of cells in vitro and for later implantation in vivo. The bioreactor comprises a chamber in which the scaffold is suitably held so that flow is not restricted. The scaffold may be stimulated at any time in the process by the probe. The stimulation can be mechanical, electrical or chemical. Ports connected to the vessel allow the flow of culture medium or fluid containing cells. A first port (Port A) is located above the scaffold, a second port (Port B) is located below the scaffold as shown in FIG. 4. Controlled flow may be generated in a downward direction through the scaffold by pumping fluid into Port A and removing fluid from Port B. To generate flow through the scaffold in the upward direction, fluid is pumped into Port B and removed from Port A.

Example 3

Figure 5:
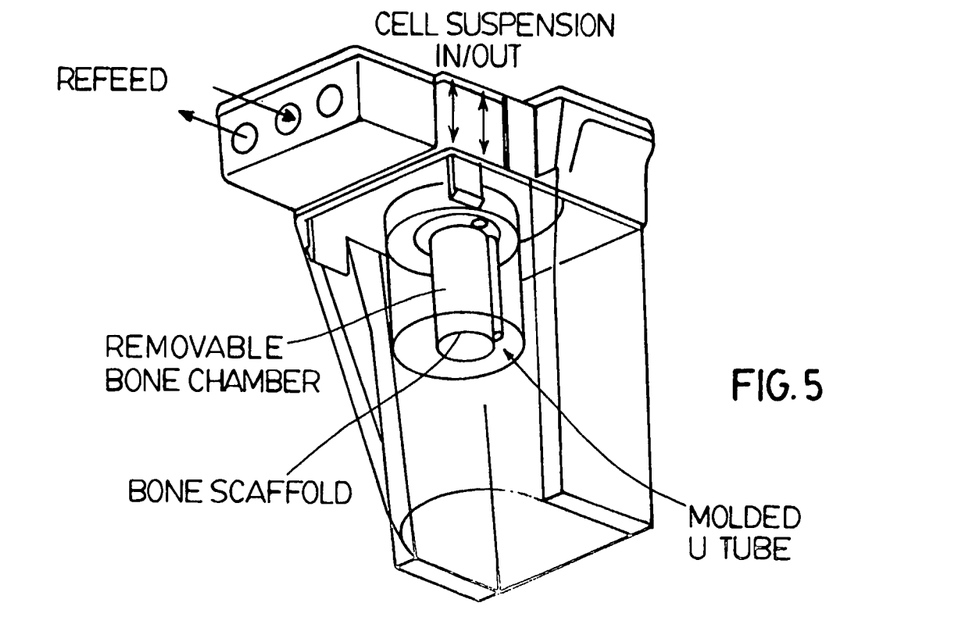
FIG. 5 shows a disposable bioreactor for culturing tissue engineered implants.

Disposable Bioreactor for Seeding and Culturing Clinical Tissue Engineered Implants A bioreactor for clinical tissue engineering comprises an assembly which is provided sterile for each patient and is disposed of after use, shown in FIG. 5, and an instrument into which one or more assemblies can be installed. The bioreactor is preloaded with a scaffold suitable for the patient indications, including defect size etc. The assembly contains the necessary fluid handling components tubes valves, vents etc for the seeding and culturing. The instrument provides the control logic for the process and pumping and actuation mechanisms to move the fluids. Autologous cells taken from the patient are added to the bioreactor assembly at the start of the process, afterwards the process of seeding and culturing the scaffold proceeds under full automatic control of the instrument until the scaffold has reached the state where it can be implanted. The chamber containing the scaffold can at this point be removed from the assembly and is transferred directly to the operating theater.

Although preferred embodiments of the invention have been described herein in detail, it will be understood by those skilled in the art that variations may be made thereto without departing from the spirit of the invention or the scope of the appended claims.

The invention claimed is:

1. A method for seeding and/or proliferating cells throughout a three-dimensional scaffold, the method comprising:
    perfusing a volume of cells in a first direction through said scaffold; and subsequently perfusing said volume of cells in the opposite direction to the first direction through said scaffold for a time sufficient to seed and proliferate said cells consistently throughout said scaffold,
    wherein said perfusing is done continuously or intermittently and along more than one axis in each of said first and opposite direction through said scaffold during perfusing through said scaffold.

2. The method of claim 1, wherein said perfusing provides multi-directional flow along said different axes through said scaffold.

3. The method of claim 1, wherein said perfusing is done at a velocity from about 0.001 mm/sec to about 10 mm/sec.

4. The method of claim 1, wherein said perfusing is done at a velocity that is kept constant.

5. The method of claim 1, wherein said perfusing is done at a velocity that is progressively increased.

6. The method of claim 1, wherein said perfusing is done at a velocity that is progressively decreased.

7. The method of claim 1, wherein said cells are selected from the group consisting of bone marrow stromal cells (BMSC), adipose derived stem cells (ADSC), periosteal cells, chondrocytes, osteoblasts, urothelial cells, other attachment dependent cells and combinations thereof.

8. The method of claim 1, wherein said scaffold is a material selected from the group consisting of biocompatible metallics, ceramics, polymers, and composite materials consisting of phosphate(s), bioactive glass(es), bioresorbable polymer(s), biocompatible metals and metallic alloys and combinations of such materials.

9. The method of claim 8, wherein said ceramic comprises calcium phosphate materials.

10. The method of claim 9, wherein said calcium phosphate comprises hydroxyapatite, calcium hydroxyapatite and an isolated bioresorbable biomaterial compound comprising calcium, oxygen and phosphorous, where a portion of at least one of these elements is substituted with an element having an ionic radius of approximately 0.1 to 0.6 Å.

11. The method of claim 1, wherein said volume of cells additionally comprises a biological agent and/or a pharmaceutical agent.

12. The method of claim 1, wherein said scaffold is provided within a bioreactor.

13. The method of claim 1, wherein sensors are provided to sense flow of said volume of cells.

14. A method for loading cells directly throughout a three-dimensional porous scaffold, the method comprising:
 (a) perfusing a volume of cells at a first velocity through said scaffold in a first direction and then in a second direction through said scaffold, wherein said second direction is substantially opposite to said first direction;
 (b) repeating (a) for a period of time sufficient for said cells to seed and proliferate throughout said scaffold; and
 (c) repeating (a) at a second velocity, which is less than said first velocity, for a further period of time sufficient for said cells to differentiate throughout said scaffold.

15. The method of claim 14, wherein said perfusing is done continuously.

16. The method of claim 14, wherein said perfusing is done intermittently.

17. The method of claim 14, wherein said first and second velocity can be from about 0.001 mm/sec to about 10 mm/sec.

18. The method of claim 14, wherein said cells are selected from the group consisting of bone marrow stromal cells (BMSC), adipose derived stem cells (ADSC), periosteal cells, chondrocytes, osteoblasts, urothelial cells, other attachment dependent cells and combinations thereof.

19. The method of claim 14, wherein said scaffold is a material selected from the group consisting of biocompatible metallics, ceramics, polymers, and composite materials consisting of phosphate(s), bioactive glass(es), bioresorbable polymer(s), biocompatible metals and metallic alloys and combinations of such materials.

20. The method of claim 19, wherein said ceramic comprises calcium phosphate materials.

21. The method of claim 20, wherein said calcium phosphate materials comprise hydroxyapatite, calcium hydroxyapatite and an isolated bioresorbable biomaterial compound comprising calcium, oxygen and phosphorous, where a portion of at least one of these elements is substituted with an element having an ionic radius of approximately 0.1 to 0.6 Å.

22. The method of claim 14, wherein (c) comprises repeating (a) and (b) with a different volume and/or type of cells.

23. The method of claim 22, wherein (c) is further repeated.

24. The method of claim 14, wherein said volume of cells additionally comprises a biological agent and/or a pharmaceutical agent.

25. A method for making an osteoinductive three-dimensional implant, the method comprising:
 perfusing a volume of bone marrow nucleated cells in substantially alternate directions and along different axes through a porous three-dimensional scaffold for a period of time sufficient for said bone marrow nucleated cells to differentiate into osteoprogenitor cells that seed within said scaffold and proliferate throughout said scaffold forming said implant.

26. A method for making a three-dimensional tissue implant comprising expanded cells provided substantially throughout said implant, the method comprising:
 (a) harvesting cells from a tissue biopsy;
 (b) perfusing said cells in alternate directions and along different axes through a porous three-dimensional scaffold without prior expansion to load said cells within said scaffold; and
 (c) repeating (b) for a time period sufficient for said cells to proliferate and differentiate within said scaffold to form said implant.

* * * * *

UNITED STATES PATENT AND TRADEMARK OFFICE
CERTIFICATE OF CORRECTION

PATENT NO.      : 8,546,142 B2                                        Page 1 of 1
APPLICATION NO. : 11/658751
DATED           : October 1, 2013
INVENTOR(S)     : Martin et al.

It is certified that error appears in the above-identified patent and that said Letters Patent is hereby corrected as shown below:

On the Title Page

Replace [73] Millenium Biologix Technologies Inc., Kingston, Ontario (CA),

Item [73] should read Assignee: Octane Biotech Inc., Kingston, Ontario (CA)

Signed and Sealed this
Second Day of December, 2014

Michelle K. Lee
*Deputy Director of the United States Patent and Trademark Office*